US010695386B2

(12) United States Patent
Morris

(10) Patent No.: US 10,695,386 B2
(45) Date of Patent: Jun. 30, 2020

(54) SKIN MICROBIOME COLONIZER FORMULATIONS AND METHODS FOR USE

(71) Applicant: Shayne K. Morris, Ogden, UT (US)

(72) Inventor: Shayne K. Morris, Ogden, UT (US)

(*) Notice: Subject to any disclaimer, the term of this patent is extended or adjusted under 35 U.S.C. 154(b) by 0 days.

(21) Appl. No.: 15/976,029

(22) Filed: May 10, 2018

(65) Prior Publication Data
US 2018/0325968 A1 Nov. 15, 2018

Related U.S. Application Data

(60) Provisional application No. 62/504,693, filed on May 11, 2017, provisional application No. 62/666,456, filed on May 3, 2018.

(51) Int. Cl.
| | |
|---|---|
| *A61K 45/00* | (2006.01) |
| *A61K 39/02* | (2006.01) |
| *A61K 49/00* | (2006.01) |
| *A61K 35/747* | (2015.01) |
| *A61K 35/745* | (2015.01) |
| *A61K 35/744* | (2015.01) |
| *A61K 9/00* | (2006.01) |
| *A61K 35/741* | (2015.01) |
| *A61K 35/76* | (2015.01) |
| *A61K 47/44* | (2017.01) |
| *A61K 47/18* | (2017.01) |
| *A61K 47/22* | (2006.01) |
| *A61K 47/08* | (2006.01) |
| *A61K 47/10* | (2017.01) |
| *A61K 47/42* | (2017.01) |
| *A61K 47/26* | (2006.01) |
| *A61K 47/36* | (2006.01) |
| *C12N 7/00* | (2006.01) |
| *A61K 35/742* | (2015.01) |
| *A61K 35/00* | (2006.01) |

(52) U.S. Cl.
CPC .......... *A61K 35/747* (2013.01); *A61K 9/0014* (2013.01); *A61K 9/0053* (2013.01); *A61K 35/741* (2013.01); *A61K 35/742* (2013.01); *A61K 35/744* (2013.01); *A61K 35/745* (2013.01); *A61K 35/76* (2013.01); *A61K 47/08* (2013.01); *A61K 47/10* (2013.01); *A61K 47/18* (2013.01); *A61K 47/22* (2013.01); *A61K 47/26* (2013.01); *A61K 47/36* (2013.01); *A61K 47/42* (2013.01); *A61K 47/44* (2013.01); *C12N 7/00* (2013.01); *A61K 2035/115* (2013.01); *C12N 2795/10132* (2013.01); *C12N 2795/10232* (2013.01); *C12N 2795/10332* (2013.01)

(58) Field of Classification Search
CPC ........ A61K 39/00; A61K 45/00; A61K 47/00; A61K 49/00; A01N 63/00
USPC ......... 424/9.1, 9.2, 93.1, 93.4, 184.1, 234.1, 424/278.1
See application file for complete search history.

(56) References Cited

U.S. PATENT DOCUMENTS

| | | | |
|---|---|---|---|
| 6,468,525 | B1 | 10/2002 | Watson et al. |
| 7,214,370 | B2 | 5/2007 | Naidu |
| 8,309,073 | B2 | 11/2012 | Mayra-Makinen et al. |
| 8,318,152 | B2 | 11/2012 | Lin |
| 8,460,648 | B2 | 6/2013 | Borody |
| 8,815,538 | B2 | 8/2014 | Lanzalaco et al. |
| 9,370,476 | B2 | 6/2016 | Kleinberg et al. |
| 2003/0180260 | A1 | 9/2003 | Clancy et al. |
| 2008/0267933 | A1 | 10/2008 | Ohlson et al. |
| 2009/0110664 | A1 | 4/2009 | Moore |
| 2010/0316769 | A1 | 12/2010 | Czarnecki-Maulden et al. |
| 2012/0087895 | A1 | 4/2012 | Mazmanian et al. |
| 2013/0273155 | A1 | 10/2013 | Yonak et al. |
| 2013/0288261 | A1 | 10/2013 | Walter et al. |

FOREIGN PATENT DOCUMENTS

| | | |
|---|---|---|
| WO | WO2011096809 | 8/2011 |
| WO | WO2014075745 | 5/2014 |
| WO | WO2014127351 | 8/2014 |

OTHER PUBLICATIONS

Skin microbiome in atopic dermatitis (AD): Interactions between bacteria (Staphylococcus) and fungi (Alternaria) M. Hammond, J. Chandra, M. Retuerto, R. Sherif, M. Ghannoum, S. Nedorost and PK Mukherjee Dermatology, Case Western Reserve University, Cleveland, OH, Journal of Investigative Dermatology (2016), vol. 136.
Salava and Lauerma Clinical and Translational Allergy 2014, 4:33 http://www.ctajournal.com/content/4/1/33.
The New England Journal of Medicine, Endogenous Antimicrobial Peptides and Skin Infections in Atopic Dermatitis, Peck Y. Ong, MD, Takaaki Ohtake, MD, PhD, Corinne Brandt, S.S., Ian Strickland, PhD, Mark Boguniwicz, MD, Tomas Ganz, MD, PhD, Richard L. Gallo, MD, PhD, and Donald Y.M. Leung, MD, PhD, vol. 347, No. 15, Oct. 10, 2002.
J Invest Dermatol, *Staphylococcus aureus* exploits epidermal barrier defects in atopic dermatitis to trigger cytokine expression, Teruaki Nakatsuji, Tiffany H. Chen, Aimee M. Two, Kimberly A. Chun, Saisindhu Narala, Raif S. Geha, Tissa R. Hata, and Richard L. Gallo, Nov. 2016, 136(11): 2192-2200.
Current Pharmaceutical Biotechnology, M.C.F Bastos, H. Ceotto, M.L.V. Coelho and J.S. Nascimento, Staphylococcal Antimicrobial Peptides: Relevant Properties and Potential Biotechnological Applications, 2009, vol. 10, pp. 38-61.

(Continued)

*Primary Examiner* — Rodney P Swartz
(74) *Attorney, Agent, or Firm* — Pate Baird, PLLC

(57) ABSTRACT

A system for treating and maintaining the health of the skin of a user. The system may include a topical formulation and an oral formulation. The topical formation may include various probiotic organisms selected for enhancing and treating the skin of a user. The oral formulation may include various probiotic organisms for enhancing and treating the skin of the user. The topical formulation and the oral formulation may be used cooperatively and simultaneously to produce a beneficial, synergistic effect.

16 Claims, 2 Drawing Sheets

(56) References Cited

OTHER PUBLICATIONS

Pediatr Res., Lactobacillus rhamnosus GG and its SpaC adhesin modulate inflammatory responsiveness and TLR-related gene expression in the fetal human gut, Kriston Ganguli, Maria Carmen Collado, Jaana Rautava, Lei Lu, Reetta Satokari, Ingemar von Ossowski, Justus Reunanen, Willem M. de Vos, Airi Palva, Erika Isolauri, Seppo Salminen, W. Allan Walker, and Samuli Rautava, Apr. 2015; 77(4): pp. 528-535.

Clin Exp Allergy, No effects of probiotics on atopic dermatitis in infancy; a randomized placebo-controlled trial, Brouwer ML, Wolt-Plompen SA, Dubois AE, van der Heide S, Jansen DF, Joijer MA, Kauffman HF, Duiverman EJ, Jul. 2006 36(7); pp. 899-906.

European Journal of Allergy and Clinical Immunology, Randomized, placebo-controlled trial of Lactobacillus rhamnosus GG as treatment of atopic dermatitis in infancy, c. Gruber, M. Wendt, C. Sulser, S. Lau, M. Kulig, U. Wahn, T. Werfel, B. Niggermann, Oct. 4, 2007.

BR J Dermatol, Prospective, randomized controlled trial on Lactobacillus rhanmosus in infants with moderate to severe topic dermatitis, Folster-Holst R, Muller F, Schnopp N, Abeck D, Kreiselmaier I, Lenz T, von Ruden U, Schrezenmeir J, Christophers E, Weichenthal M, Dec. 2006 155(6).

BMC Genomics, Antagonism between *Staphylococcus epidermidis* and Propionibacterium acnes and its genomic basis, Gitte J.M. Christensen, Christian F.P. Scholz, Jan Enghild, Holger Rohde, Mogens Kilian, Andrea Thumer, Elzieta Brzuszkiewicz, Hans B. Lomholt and Holger Bruggemann, Feb. 2016 17:152.

Appl Microbiol Biotechnol, *Staphylococcus epidermidis* in the human skin microbiome mediates fermentation to inhibit growth of Propionibacterium acnes: Implications of probiotics in acne vulgaris, Yanhan Wang, Sherwin Kuo, Muya Shu, Jinghua Yu, Stephen Huang, Ashley Dai, Aimee Two, Richard L. Gallo, and Chung-Ming Huang, Jan. 2014; 98(1).

Eur. J. Immunol., Lactobacillus casei reduces $CD8_+$ T cell-mediated skin inflammation, Ludivine Chapat, Karine Chemin, Bertrand Dubois, Raphaelle Bourdet-Sicard, and Dominique Kaiserlian, 2004, v. 34, pp. 2520-2528.

Semin Cutan Med Surg., Antimicrobial Peptides, Skin Infections and Atopic Dermatitis, Tissa R. Hata, MD and Richard L. Gallo, MD, Jun. 2008; 27(2); pp. 144-150.

International Journal of Probiotics and Prebiotics, Probiotics to young children with atopic dermatitis: A randomized placebo-controlled trial, R. Gobel, N. Larsen, C Molgaard, M Jakobsen, and KF Michaelsen, Apr. 2010 vol. 5, No. 2, pp. 53-60.

Annals of Nutrition & Metabolism, Probiotics in the Treatment and Prevention of Atopic Dermatitis, R. Folster-Holst, Sep. 8, 2010; 57(suppl 1):16-19.

British Journal of Dermatology, The role of the skin microbiome in atopic dermatitis: a systematic review, R.D. Bjerre, J. Bandier, L. Skov, L. Engstrand, and J.D. Johansen, 2017 vol. 177, pp. 1272-1278.

| Organism | Month0 CFU's | Month3 CFU's | Month6 CFU's | Month9 CFU's | Month12 CFU's |
|---|---|---|---|---|---|
| Bacillus lichinformis | 1.35E+10 | 7.00E+09 | 4.90E+09 | 2.90E+09 | 1.20E+09 |
| Bifidobacterium breve | 4.00E+09 | 1.00E+09 | 1.88E+07 | 8.80E+06 | 4.80E+06 |
| Bifidobacterium infantis | 7.00E+09 | 1.63E+07 | 7.00E+06 | 2.00E+06 | 5.70E+05 |
| Lactobacillus fermentum | 4.25E+10 | 1.00E+09 | 6.10E+08 | 6.10E+08 | 6.10E+08 |
| Lactobacillus rhamnosus | 2.00E+09 | 5.20E+07 | 7.40E+07 | 4.00E+06 | 3.70E+06 |
| Lactobacillus sakei | 8.50E+10 | 1.00E+09 | 1.80E+08 | 1.80E+08 | 1.80E+08 |
| Lactobacillus paracasei | 1.80E+10 | 5.00E+09 | 1.54E+09 | 4.00E+08 | 6.54E+07 |
| Staphlococcus epidermidis | 1.00E+09 | 2.00E+09 | 2.90E+09 | 5.00E+08 | 2.00E+08 |
| Staphlococcus xylosus | 1.00E+09 | 2.00E+09 | 2.90E+09 | 3.90E+09 | 3.40E+08 |
| Lactococcus lactis | 1.00E+09 | 3.00E+08 | 1.20E+08 | 8.00E+07 | 2.00E+07 |
| Bifidobacterium bifidum | 4.00E+08 | 1.20E+08 | 3.90E+08 | 9.00E+07 | 6.50E+07 |
| Lactobacillus plantarum | 3.00E+08 | 5.50E+07 | 2.00E+07 | 1.70E+07 | 2.00E+06 |
| Complex Probiotic | 2.00E+10 | 1.00E+10 | 5.00E+10 | 2.00E+10 | 1.60E+09 |

Figure 1

SKIN MICROBIOME COLONIZER FORMULATIONS AND METHODS FOR USE

RELATED APPLICATIONS

The application claims the benefit of U.S. Provisional Patent Application Ser. No. 62/504,693 filed on May 11, 2017, and U.S. Provisional Patent Application Ser. No. 62/666,456 filed on May 3, 2018, both of which are hereby incorporated by reference in their entireties.

BACKGROUND

1. Field of Invention

This invention relates to formulations and methods of use for topical and oral supplement probiotics, and more specifically for topical oil products containing probiotics and oral supplement products containing probiotics used in combination to provide more beneficial, synergistic results.

2. Background

Microbes are present in every environmental niche and live in close association with humans and each other. Members of these communities may include bacteria, archaea, viruses, fungi, and protists.

In humans and animals, microbes may provide protection against foreign invaders, educate and stimulate the immune response, produce antimicrobials, aid in digestion, and produce vitamins, among a host of other functions. This field of research is defined as the human microbiome. Microbes may be present in numerous areas of the human body, including without limitation, the skin, the mouth, and the gut.

The skin represents the primary interface between the host and the environment. This organ is also home to trillions of microorganisms that play an important role in tissue homeostasis and local immunity. In general, resident and transient microbial species are present on the skin.

The term resident refers to viable, reproducing populations, whereas transient species have no capacity for sustained growth and reproduction in the cutaneous environment. Resident microbial species include at least Proprionibacteria, Coagulase-negative Staphylococci, Micrococci, Corynebacteria and *Acinetobacter*. Notably the human skin microbiota is complex and in fact comprises approximately one hundred and thirteen (113) phylotypes that belong to six bacterial divisions. Among these, Proteobacteria dominate the skin microbiota. In aggregate, preservation of the resident microflora is thought to be an effective way to achieve maintenance of healthy, normal skin functions.

Some of the physical factors defined by the host environment include the number and size of follicles and glands, gland function, and the flow of secretions. Another level of complexity is provided by the interplay between skin microorganisms and the skin immune system. The skin possesses the capacity to mount both innate and adaptive immune responses. There is increasing evidence that the skin microflora modulates the immune responses. In the context, it is important to state that skin microflora, skin barrier function and the skin immune system are closely linked to each other and appear to form a complex and highly regulated network that controls a variety of fundamental skin functions. It can be beneficial to make attempts to selectively manipulate this system in order to achieve beneficial effects for human skin.

Skin microbiota research continues to elucidate the relationship between the microorganisms and the skin associated immune system. When the "healthy" skin microorganisms are in balance, it may be referred to as "eubiosis." When the "healthy" skin microorganisms are no longer in balance and pathogenic organisms take up residency disrupting the balance, it may be referred to as "dysbiosis." During periods of dysbiosis, inflammation, irritation, and lesions of the skin may ensue. For example and not by way of limitation, eczema, atopic dermatitis, rosacea and acne vulgaris, or the like, may arise on the skin.

*Staphylococcus epidermidis*, or *S. epidermidis*, is a major constituent of the normal microflora on healthy, human skin. *S. epidermidis* acts as a barrier against colonization of potentially pathogenic microbes and against overgrowth of already present opportunistic pathogens. Put another way, *S. epidermidis* is a key factor in preventing dysbiosis. *S. epidermidis* regulates skin homeostasis and suppresses the pathogenic inflammation that is induced by *Propionibacterium acnes*, or *P. acnes*.

Commensals, or normal skin resident microbes, dominantly affect skin immunity and identify the cellular mediators involved in this specification. In particular, colonization with *S. epidermidis* induces IL-17A+ CD8+ T cells that are normally found on the epidermis and help enhance innate barrier immunity and limit pathogen invasion.

*S. epidermidis* is the dominant commensal bacterium cultured from the skin microflora and produces various types of bacteriocins. *S. epidermidis* produces a variety of molecules that have antimicrobial activity. For example, peptides called phenosoluble modulins demonstrate selective activity against *S. aureus*, group A Streptococci, and *Escherichia coli*, but not against other bacteria. Most of these peptides are encoded in plasmids. Epidermin, Pep 5, and epilancin K7 are the most characterized or common bacteriocins isolated from *S. epidermidis*.

*Lactobacillus* and *Bifidobactrium* contribute to a healthy skin microbiota. One study compared the skin microbiomes for allergic (positive skin prick test for food antigens) and non-allergic children. This study found lower counts of *Lactobacillus* and *Bifidobactrium* and higher counts of *Staphylococcus aureus* and *Enterobacteria* on the skin in the group of allergic children.

It would be beneficial to develop and use a product that maintains, protects, and enhances eubiosis. Such a product may include a topical product that colonizes the user's skin with the desirable microbes, or a nutritional supplement product that promotes healthy skin, or a combination of such products.

BRIEF SUMMARY OF THE INVENTION

In accordance with the foregoing, certain embodiments of a formulation, compound, combination, and method of use in accordance with the invention provide a skin microbiome colonizer product and/or an edible nutritional supplement product that can be utilized separately and in combination to provide a user, or subject, a variety of health benefits, including increased skin healing and health maintenance.

In one embodiment, a product may selectively affect a user's skin through the use of prebiotic and probiotic applications. A product may contain a synergistic blend of prebiotic lipids, commensal bacteria, and probiotic transient bacteria that dominantly and beneficially affect skin immunity, health and eubiosis.

In one embodiment, the product development process may include three (3) distinct steps: (1) development of the prebiotic lipid formula; (2) discovery of the probiotic organisms that affect skin health and reverse dysbiosis and skin disease; and (3) combining the prebiotic formula and probiotic organisms into a topical product and an oral dose product.

In one embodiment, the prebiotic lipid formula and probiotic organisms included in a topical product may substantively match the prebiotic lipid formula and probiotic organisms included in an oral dose product. In another embodiment, the prebiotic lipid formula and probiotic organisms included in a topical product may have slightly adjusted ratios as compared to the prebiotic lipid formula and probiotic organisms included in an oral dose product. In another embodiment, the prebiotic lipid formula and probiotic organisms included in a topical product may be separate and distinct as compared to the prebiotic lipid formula and probiotic organisms included in an oral dose product.

In one embodiment, a system for treating the skin of a user may comprise a topical formulation that may be described as comprising two parts or components: an oil matrix and a topical probiotic group. An oil matrix may comprise effective amounts of jojoba oil, beeswax oil, borage oil, hemp oil, kukui oil, marula oil, perillia oil, grape seed oil, Sea Buckthorn oil, ceramides, tocopherals, vanillin, coconut oil, and vitamin D, or any combination thereof. An oil matrix may be formulated so that the oil matrix is substantially identical to skin oil. A topical probiotic group may comprise effective amounts of *Bacillus licheniformis, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis,* and *Staphylococcus xylosus*, or any combination thereof.

In one embodiment, a system for treating the skin of a user may comprise an oral oral formulation that may be described as comprising two parts or components: a prebiotic matrix and an oral probiotic group. A prebiotic matrix may comprise effective amounts of Igy-immunoglobulin, fructooligosaccharides, deoxnoiirimycin polysaccharide (DPM), carotenoids, and polyphenolic, or any combination thereof. An oral probiotic group may comprise effective amounts of *Bacillus licheniformis, Bifidobacterium bifidum, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis,* and *Staphylococcus xylosus*, or any combination thereof.

Pronounced antibacterial activities of *Lactobacillus reuteri* have been attributed to the production of organic acids. Such results suggest that *L. reuteri* may be a useful probiotic agent to prevent acne and to control the growth of bacteria involved in acne inflammation.

Additionally, *Lactobacillus plantarum*, a gram-positive bacterium that produces antimicrobial peptides, may act like an anti-inflammatory and enhance the antimicrobial properties of the skin when applied to the skin. Certain clinical studies have been conducted to determine the effect of *Lactobacillus* extract on the improvement of the skin barrier and the reduction of erythema from chemical irritants, skin microflora, and acne. Results have shown that *Lactobacillus* extract was effective in reducing skin erythema, repairing the skin barrier, and reducing skin dysbiosis, thereby exhibiting an effective reduction in acne lesion size and erythema.

BRIEF DESCRIPTION OF THE DRAWINGS

The foregoing features of the present invention will become more fully apparent from the following description and appended claims, taken in conjunction with the accompanying drawings and experimental data. Understanding that these drawings and data depict only typical embodiments of the invention and are, therefore, not to be considered limiting of its scope, the invention will be described with additional specificity and detail through use of the accompanying drawings and data in which:

FIG. 1 illustrates a table providing results of stability testing to confirm the long term viability of an embodiment of a skin colonizer.

DETAILED DESCRIPTION OF THE PREFERRED EMBODIMENTS

Figure 2:
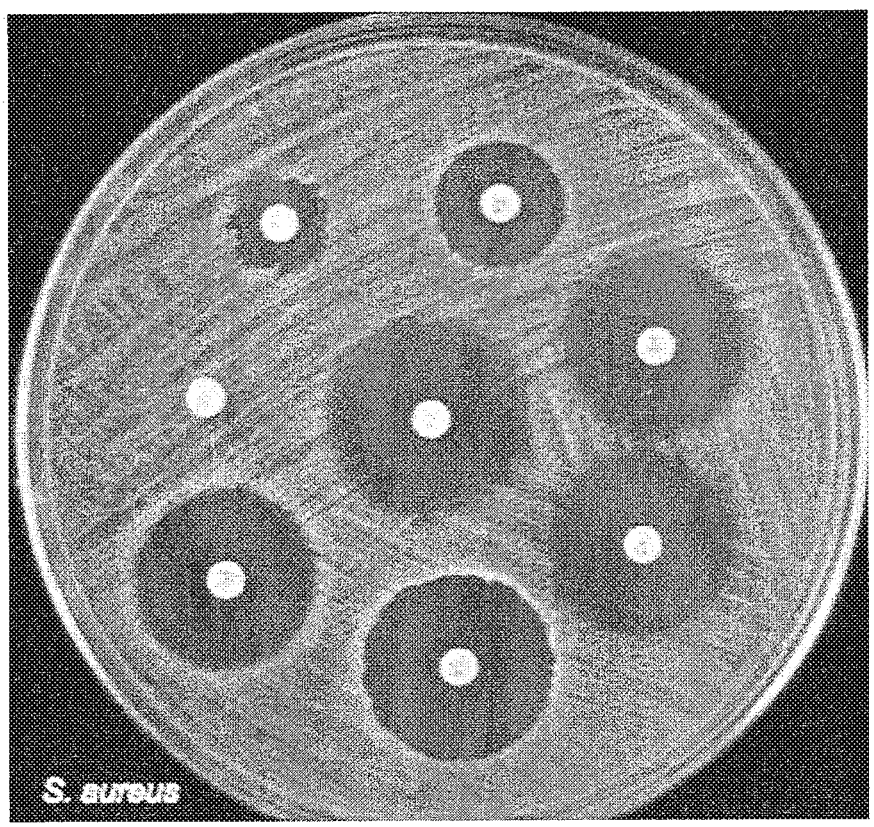
FIG. 2 illustrates probiotic inhibition of *S. aureus*.

It will be readily understood that the components of the present invention, as generally described herein, could be arranged and designed in a wide variety of different configurations or formulations. Thus, the following more detailed description of the embodiments of the system, product and method of the present invention, is not intended to limit the scope of the invention, as claimed, but is merely representative of various embodiments of the invention.

In one embodiment, a system for improving or maintaining the health of the skin of a person may include a topical product and an oral nutritional supplement product. In order for the system to work at its best, the two products may be harmonized. Such harmonization may include harmonizing each of the respective products to the separate and distinct body environments intended for each, as well as harmonizing the respective products to each other.

Sebum is produced by mammalian sebaceous glands and may including the following components: squalene, cholesterol esters, cholesterol, triglycerides, diglycerides, monoglycerides, wax mono-esters, wax di-esters, free fatty acids, and parafins. Skin keritinocytes may also produce a hydrolipid fluid primarily released in areas of the skin that lack sebaceous glands. Hydrolipid secretion may be composed of phospholipids, sphingolipids, free fatty acids and cholesterol. One important function of both sebum and hydrolipids is to nourish the skin microbiota.

Therefore, it may be considered important to produce a plant based version of the lipid for use in a topical application for a skin microorganism prebiotic formulation. A topical oil formula has been tested using over 20 probiotic microorganisms and can sustain in a state of stasis many of these organisms. While a product or formulation may contain any number of probiotic organisms, eleven (11) probiotic organisms were used in one embodiment based on their positive impact on skin. An embodiment such as this has been the focus of research on skin health and disease reduction, however, the majority of the research is based on consuming such an embodiment orally.

One aspect of the present invention is that a similar embodiment may be used topically. Another aspect of the present invention is that the combined, coordinated, simultaneous use of a topical formulation and an oral formulation can be most effective and produce synergistic results.

Each of the organisms considered may be individually tested for survival in single oils before moving the organisms into a combination of oils. Such oils may include: jojoba, grape seed, perillia, marula, kukui, hemp and borage. For example and not by way of limitation, beeswax may first be melted and then added into jojoba oil. This may allow the wax to dissolve permanently in the oil. Low concentration oils are weighed separately, such as, sea buckthorn, vitamin D, tocotrienols, and coconut oil.

In one embodiment, a topical formulation using plant oils and natural waxes may be assembled to approximate the sebum or hydrolipid layer. For example and not by way of limitation, a prebiotic lipid base formulation may be described as the following:

TABLE 1

| | |
|---|---|
| Jojoba | 60.0-80.0% |
| Grape Seed | 0.10-4.00% |
| Perillia | 0.10-5.00% |
| Marula | 0.10-2.00% |
| Kukui | 0.10-2.00% |
| Hemp | 0.10-2.00% |
| Borage | 0.10-2.00% |
| Beeswax | 0.10-4.50% |
| Sea Buckthorn | 0.10-3.50% |
| Tocopherols | 0.50-1.00% |
| Vitamin D | 0.040-0.20% |
| Coconut | 0.10-2.50% |
| Phospholipids | 0.10-10.00% |

In a separate embodiment, a topical formulation using plant oils and natural waxes may be assembled to approximate the sebum or hydrolipid layer. A topical formulation or oil matrix may be formulated to approximate, or be substantially identical to, normal, human skin oil. For example and not by way of limitation, a prebiotic lipid base formulation may be described as the following:

TABLE 2

| | |
|---|---|
| Jojoba | 60.0-80.0% |
| Grape Seed | 0.10-4.00% |
| Perillia | 0.10-5.00% |
| Marula | 0.10-2.00% |
| Kukui | 0.10-2.00% |
| Hemp | 0.10-2.00% |
| Borage | 0.10-2.00% |
| Ceramides | 0.10-4.50% |
| Beeswax | 0.10-4.50% |
| Sea Buckthorn | 0.10-3.50% |
| Tocopherols | 0.50-1.00% |
| Vitamin D | 0.040-0.20% |
| Coconut | 0.10-2.50% |
| Phospholipids | 0.10-10.00% |

A formulation similar to an embodiment described herein is not only based on matching the hydrolipid layer and sebum chemical profile, but it may also sustain all the added healthy probiotic organisms. As described, a similar formulation may include a ceramide in an appropriate amount. It has been shown a formulation similar to the one described herein may have the ability to suspend and maintain living probiotic organisms for a minimum of twelve (12) months and up to an extended two (2) year period for certain organisms.

In one embodiment, the chemical composition of the plant oils may be listed from smallest fatty acid chain to the longest fatty acid chain: caproic, C6:0; caprylic, C8:0; capric, C10:0; lauric, C12:0; myristic, C14:0; palmitic, C16:0; palmitoleic, C16:1; stearic, C18:0; oleic, C18:1; linoleic, C18:2; linolenic, C18:3; arachidic, C20:0; eicosenoic, C20:1; behenic, C22:0; erucic, C22:1; lignoceric, C24:0. In one embodiment, the wax composition may include the following: hydrocarbons, mono-esters, di-esters, tri-esters, hydroxyl-mono-esters, phospholipids, hydroxyl polyesters, fatty acids, and fatty alcohols.

In one embodiment, a product including skin microbiota probiotic may be utilized. The individual organisms may be tested using a skin prebiotic formula oil to track and evaluate individual viability. Table 3 below follows six (6) months of each organism being incubated and then plated under specific conditions and selective agar to ensure accurate count tracking.

TABLE 3

| Organism | Month 1 CFU's | Month 2 CFU's | Month 3 CFU's |
|---|---|---|---|
| Bacillus licheniformis | 1.35E+10 | 7.00E+08 | 4.90E+09 |
| Bifidobacterium breve | 4.00E+08 | 1.00E+08 | 1.88E+07 |
| Bifidobacterium infantis | 7.00E+08 | 1.63E+07 | 1.00E+07 |
| Lactobacillus fermentum | 4.25E+10 | 1.00E+09 | 6.10E+08 |
| Lactobacillus rhamnosis | 2.00E+09 | 5.20E+06 | 1.40E+07 |
| Lactobacillus sakei | 8.50E+10 | 1.00E+09 | 1.80E+08 |
| Lactobacillus paracasei | 1.80E+10 | 5.00E+09 | 1.54E+09 |
| Staphlococcus epidermidis | 1.00E+09 | 2.00E+09 | 2.90E+09 |
| Lactococcus lactis | 1.00E+09 | 3.00E+08 | 1.20E+10 |
| Bifidobacterium bifidum splactis | 4.00E+08 | 1.20E+08 | 3.90E+09 |
| Lactobacillus plantarum | 3.00E+08 | 5.50E+07 | 2.00E+07 |

Table 4 below shows a viable count of each organism being incubated and then plated under specific conditions and selective agar to ensure accurate count tracking. Additionally, PCR amplification (Thermofischer QTPCR and reagents) of the microorganisms ensures accurate genus and species identification (+ or −).

TABLE 4

| Organism | Month 1 CFU's | PCR Ident+ |
|---|---|---|
| Bacillus licheniformis | 1.35E+10 | Yes |
| Bifidobacterium breve | 4.00E+08 | Yes |
| Bifidobacterium infantis | 7.00E+08 | Yes |
| Lactobacillus fermentum | 4.25E+10 | Yes |
| Lactobacillus rhamnosis | 2.00E+09 | Yes |
| Lactobacillus sakei | 8.50E+10 | Yes |
| Lactobacillus paracasei | 1.80E+10 | Yes |
| Propionibacterium jensenii | 2.20E+09 | Yes |
| Propionibacterium freudenreichii | 1.70E+09 | Yes |
| Staphlococcus xylosis | 1.10E+09 | Yes |
| Staphlococcus epidermidis | 1.00E+09 | Yes |
| Lactococcus lactis | 1.00E+09 | Yes |
| Bifidobacterium bifidum splactis | 4.00E+08 | Yes |
| Lactobacillus plantarum | 3.00E+08 | Yes |

In one embodiment, the following formulation was determined to be the most viable and effective in both in-vitro and in-vivo experiments.

Table 5 shows possible formulations as organisms per colony forming unit (CFU's) with respect to both prebiotic oil topical and oral dosages.

TABLE 5

| Organism | CFU's |
|---|---|
| Staphlococcus epidermidus | $1.0 \times 10^2$-$1.0 \times 10^9$ |
| Bacillus licheniformis | $5.0 \times 10^4$-$500 \times 10^7$ |
| Bifidobacterium breve | $1.0 \times 10^6$-$50 \times 10^9$ |
| Bifidobacterium infantis | $1.0 \times 10^6$-$19 \times 10^9$ |
| Lactobacillus fermentum | $36 \times 10^5$-$40 \times 10^9$ |
| Lactobacillus rhamnosis | $39 \times 10^5$-$80 \times 10^9$ |
| Lactobacillus sakei | $85 \times 10^5$-$10 \times 10^9$ |
| Lactobacillus paracasei | $40 \times 10^5$-$50 \times 10^9$ |
| Propionibacterium jensenii | $1.0 \times 10^2$-$50 \times 10^9$ |
| Propionibacterium freudenreichii | $1.0 \times 10^2$-$50 \times 10^9$ |
| Lactococcus lactis | $19 \times 10^5$-$1 \times 10^9$ |
| Bifidobacterium bifidum | $10 \times 10^5$-$1 \times 10^9$ |
| Lactobacillus plantarum | $10 \times 10^5$-$1 \times 10^9$ |
| Staphlococcus xylosus | $10 \times 10^5$-$1 \times 10^9$ |

In one embodiment, a possible formulation of organisms may include a phage, or bacteriophage, in either or both of a topical formulation and an oral formulation. For example and not by way of limitation, a topical formulation or an oral formulation may include bacteriophages infecting *Propionibacterium acnes*, which are classified as Siphoviruses, or Siphoviridae. As another example, a topical formulation or an oral formulation may include bacteriophages infecting *Staphylococcus aureus*, which have been classified as part of families such as Podoviridae, which have a very short tail, Siphoviridae, which have a long non-contractile tail, and Myoviridae, which have a long, contractile, double-sheathed tail. The bacteriophage may be of a type that infects, attacks or destroys an organism or bacteria that promotes or contributes to dysbiosis, whether on a skin surface or in the gut. Thus, a bacteriophage may be utilized in either or both of a topical formulation and an oral formulation.

Stability of viable probiotics in an oil prebiotic formula can be important and tricky, since probiotics are inherently unstable. Therefore, creating a stable topical formulation can be very unique and critical to deliver living probiotic organisms to the skin. In order to better study each organism in detail, a vial of a prebiotic was made using a single organism in order to study its stability without interference. A combination formula was also made to look for any possible effects from competition, combinatorial effects, or the like. Utilizing a formulation like that described herein, stability was assessed over time points beginning at time zero and continuing for twelve (12) months. Samples were kept at room temperature and a sample was taken at each time point, plated on selective media, grown anaerobically and enumerated.

Referring to FIG. 1, results of stability testing confirm the long term, including over 12-month, viability of an embodiment of a skin colonizer. In another embodiment, a range of probiotic concentrations may be utilized to engineer and pre-determine the life of a product embodiment. In another embodiment, a skin colonizer formulation may be capable of stabilizing the probiotics long enough and at a high enough level to make an effective formulation for human use.

In one embodiment, an important aspect of the system described herein may be that the topical skin microbiota formulation and the oral dose formulation use the same, or effectively the same, commensal and transient probiotic organisms. Certain studies support the concept of oral probiotics affecting skin health. The most likely mechanism may be through tight junction integrity and immune system interactions where T-helper cells are educated.

Herein is shown how embodiments that utilize a synergistic blend of organisms in the skin microbiome topical and oral demonstrate the ability to improve skin hydration, texture, correct dysbiosis, and improve eubiosis. Together these actions improve skin related issues, such as atopic dermatitis, rosacea, psoriasis, acne vulgaris, and the like.

In one embodiment, an oral doseable form, or capsule, may be taken at the same time a corresponding topical formulation is applied for full or enhanced efficacy.

When a selection of organisms is blended into an oral dosage formulation, it may be necessary and beneficial to add a prebiotic matrix in order to maintain viability and transit through the gastrointestinal tract. In one embodiment, a prebiotic matrix may be comprised of the following: IgY-immunoglobulin, fructooligosaccharides, deoxnoiirimycin polysaccharide (DPM), carotenoids, and polyphenolic compounds.

Table 6 provides an example of a possible embodiment of a skin microbiota topical formulation.

TABLE 6

| Oil | grams | Percentage |
|---|---|---|
| Jojoba | 22.56 | 80.00 |
| Beeswax | 0.705 | 2.50 |
| Borage | 0.564 | 2.00 |
| Hemp | 0.564 | 2.00 |
| Kukui | 0.564 | 2.00 |
| Marula | 0.564 | 2.00 |
| *Perillia* | 0.564 | 2.00 |
| Grape Seed | 0.4117 | 1.46 |
| Sea Buckthorn | 0.282 | 1.00 |
| Ceramides (oat oil) | 0.282 | 1.00 |
| Tocopherals | 0.282 | 1.00 |
| Vanillin | 0.141 | 0.50 |
| Coconut | 0.282 | 1.00 |
| Vitamin D | 0.0113 | 0.04 |
| Organisms (total) | 0.832 | 2.50 |
| *Bacillus licheniformis* | 0.000705 | |
| *Bifidobacterium breve* | 0.11515 | |
| *Bifidobacterium infantis* | 0.13395 | |
| *Lactobacillus fermentum* | 0.1269 | |
| *Lactobacillus plantarum* | 0.1269 | |
| *Lactobacillus rhamnosus* | 0.137475 | |
| *Lactobacillus sakei* | 0.11985 | |
| *Lactobacillus paracasei* | 0.0705 | |
| *Staphylococcus epidermidis* | 0.0003525 | |
| *Staphylococcus xylosus* | 0.0003525 | |

Table 7 provides an example of a possible embodiment of a skin microbiota oral dose formulation.

TABLE 7

| Organism | grams |
|---|---|
| *Bacillus licheniformis* | 0.01 |
| *Bifidobacterium breve* | 0.01 |
| *Bifidobacterium infantis* | 0.01 |
| *Bifidobacterium bifidum* | 0.10 |
| *Lactobacillus fermentum* | 0.01 |
| *Lactobacillus plantarum* | 0.01 |
| *Lactobacillus rhamnosus* | 0.01 |
| *Lactobacillus sakei* | 0.01 |
| *Lactobacillus paracasei* | 0.01 |
| *Staphylococcus epidermidis* | 0.002 |
| *Staphylococcus xylosus* | 0.002 |
| Prebiotic Matrix | |
| IgY - immunoglobulin | 0.10 |
| Fructooligosaccharides | 0.10 |
| Deoxnoiirimycin polysaccharide | 0.10 |
| Carotenoids | 0.01 |
| Polyphenolic | 0.01 |

Synergistic skin microbiota may be inhibitory towards skin pathogens in the genus *P. acnes, S. aureus, P. aruginosa,* and *S. pyogenes*. Multiple plating techniques may be used to test each of the *Lactobacillus, Bacillus, Bifidobacterium, Lactococcus,* and *Streptococcus* genera. Each organism is grown on a plate and then tested against pathogenic organisms and recorded as inhibitory by producing bacteriocins.

Referring to FIG. 2, it has been shown that *S. epidermidis, S. xylosis, L. sakei, L. paracasei, L. rhamnosis, L. fermentum,* and *B. breve* demonstrate probiotic inhibition of *S. aureus*.

In other embodiments, formulations may be adjusted with acceptable ranges to produce desired results. For example and not by way of limitation, individual components of the skin colonizer oil for the topical application may be adjusted, and other, individual probiotics may be added, deleted, or substituted.

The genus *Propionibacterium* is divided into the cutaneous and the dairy, or classical, species. Classical species include *Propionibacterium jensenii, Propionibacterium acidipropionici, Propionibacterium freudenreichii* (subspecies *freudenreichii* and *shermanii*), *Propionibacterium thoenii*. *Propionibacterium* bacteriocins with a narrow spectrum of activity targeted toward species related to strains of *Propionibacterium acnes* and *Corynebacterium parvum*.

Many strains isolated from a variety of sources inhibited the growth of *S. aureus* and clinical isolates of MRSA in vitro. The most active strains may include *Lactobacillus reuteri, Lactobacillus rhamnosus* GG, *Propionibacterium freudenreichii, Lactobacillus paracasei, Lactobacillus acidophilus, Lactobacillus casei, Lactobacillus plantarum, Lactobacillus bulgaricus, Lactobacillus fermentum*, and *Lactococcus lactis*. Their effects may be mediated both by direct cell competitive exclusion as well as production of acids or bacteriocin-like inhibitors.

A formulation of a skin colonizer embodiment has been verified to change the microbiota of an application site. For instance, an observational study was designed and performed to a skin colonizer embodiment on the skin of a user. Thirty (30) people were recruited with full consent and training on the application and testing project. First, a baseline sample was obtained from each participant at the specific site to be tested on the individual participant's body. Body sites included in the analysis included upper and lower arms, thighs, shoulders, between toes, and faces. The baseline sample represents the microbiota population on the skin before any product has been applied. Taking the sample, a specialized swab and buffer solution is used to pull the microbiota cells from the skin and preserve the DNA. In the lab, the microorganisms are identified and quantified by looking at some unique regions of the 16sRNA called variable regions. The 16sRNA first has to be amplified using PCR and then sequenced using a sequencer. The output data may represent the phylum, class, order, genus and species of the microorganisms, or microbiome, in the sample tested.

A typical baseline microbiome for a participant may be composed of approximately 9% Actinobacteria, 49% Proteobacteria, and 42% Firmicutes.

Next, each participant was given a sample of the skin colonizer embodiment and a document with complete directions on how and when to apply the skin colonizer. Samples of the participants' skin microbiomes were taken at intervals of three (3) weeks, six (6) weeks, and nine (9) weeks. The same technique was used to collect and analyze each participant's skin site microbiome.

The resulting data showed statistically significant changes in a majority of the study's participants over the range of different sites of the participants' skin that were tested. Because the skin colonizer formulation may contain *Lactobacillus, Bifidobacterium*, and *Staphylococcus*, data was evaluated for increases in the genus. When possible, a test was performed to determine whether a species used in the skin colonizer could be found on the skin of the participants.

A typical microbiome for a participant after application of the skin colonizer applied according to the directions provided and after testing may be composed of approximately 47% Actinobacteria, 47% Proteobacteria, and 6% Firmicutes.

Thus, a skin colonizer embodiment is shown to bring about a statistically significant change to the microbiota on the skin of a user, or subject. Put another way, it is shown that the microorganisms from the skin colonizer can be colonized or transplanted onto the skin and they can survive and flourish.

In one embodiment, a user may utilize a system described herein to treat or improve or maintain the health of an area of skin. A system may include a topical formulation or a skin colonizer for influencing the microbiota of an area of skin. Such a system may treat, improve, maintain, or influence a desired, intended area of the user's skin. Such a system may include multiple steps in a method or process.

One step in a possible process or method of use may be designating, choosing, or providing an area of skin having a microbiota and a state of dysbiosis. The microbiota may be composed of virtually any combination of organisms. Moreover, the microbiota may cause or influence a state of dysbiosis, or the microbiota may cause or influence a state of eubiosis.

Another step may include providing a topical skin colonizer that may comprise an oil matrix that may comprise effective amounts of jojoba oil, beeswax oil, borage oil, hemp oil, kukui oil, marula oil, perillia oil, grape seed oil, Sea Buckthorn oil, ceramides, tocopherals, vanillin, coconut oil, and vitamin D, or any appropriate combination of these components that will result in an acceptable oil matrix. An oil matrix may be formulation to be substantially equivalent, or have approximately the same composition and make up, as normal, human skin oil. The topical skin colonizer may also comprise a topical probiotic group that may comprise effective amounts of *Bacillus licheniformis, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus*, or any suitable combination of these organisms that will result in an acceptable topical probiotic group. An acceptable topical probiotic group may also include additional organisms not specified, such as *Propionibacterium jensenii, Propionibacterium freudenreichii, Roseomonas mucosa*, and the like. An acceptable topical probiotic group may also include one or more bacteriophage. A bacteriophage may be chosen that will help promote eubiosis, or put another way, a bacteriophage may be chosen that will attack those organisms that are causing or influencing dysbiosis.

Another step may include applying the topical skin colonizer to an area of skin. Applying the topical skin colonizer to a desired, selected area of the skin may be done one or more times during a day. Between approximately one (1) gram and five (5) grams of topical skin colonizer formulation may be applied depending on the size of the area of skin. Such an application process may include using a swab or some other material, and may also include the user applying the topical skin colonizer with their hand or fingers. Application of the topical skin colonizer may be accomplished in any suitable manner. Any suitable amount of the topical skin colonizer may be used and applied as desired.

Another step may include changing the microbiota of the area of skin. An appropriate topical formulation and/or an appropriate oral formulation may be utilized to bring about any desired change in the microbiota.

Another step may include the microbiota of the area of skin being changed from comprising a relatively large amount of Firmicutes and a relatively small amount of Actinobacteria, to the microbiota of the area of skin comprising a relatively large amount of Actinobacteria and a relatively small amount of Firmicutes.

Another step may include changing the state of dysbiosis to a state of eubiosis. Another step may also include maintaining a state of eubiosis.

Another step may include providing an oral formulation that may comprise a prebiotic matrix that may comprise effective amounts of Igy-immunoglobulin, fructooligosaccharides, deoxnoiirimycin polysaccharide (DPM), carotenoids, and polyphenolic, or any appropriate combination of these components that will result in an acceptable prebiotic matrix. The oral formulation may also comprise an oral probiotic group that may comprise effective amounts of *Bacillus licheniformis, Bifidobacterium bifidum, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus*, or any suitable combination of these organisms the will result in an acceptable oral probiotic group. An acceptable oral probiotic group may also include additional organisms not specified, such as *Propionibacterium jensenii, Propionibacterium freudenreichii, Roseomonas mucosa*, and the like. An acceptable oral probiotic group may also include one or more bacteriophage. A bacteriophage may be chosen that will help promote eubiosis, or put another way, a bacteriophage may be chosen that will attack those organisms that are causing or influencing dysbiosis.

Another step may include ingesting the oral formulation. The oral formulation may be ingested in any suitable manner and at any appropriate time. Generally, the oral formulation may be ingested at a time relatively close to the time when a corresponding topical formulation is applied to the user's skin. This may include a user taking or swallowing the oral formulation before or after the time when a corresponding topical formulation is applied to the user's skin. The oral formulation may be provided in any suitable form, such as a pill, paste, or the like.

Another step may include changing the microbiota of the area of skin. An appropriate topical formulation and/or an appropriate oral formulation may be utilized to bring about any desired change in the microbiota.

Another step may include the microbiota of the area of skin being changed from comprising a relatively large amount of Firmicutes and a relatively small amount of Actinobacteria, to the microbiota of the area of skin comprising a relatively large amount of Actinobacteria and a relatively small amount of Firmicutes.

Another step may include changing the state of dysbiosis to a state of eubiosis. Another step may also include maintaining a state of eubiosis.

In one embodiment, a user, or subject, may utilize a system described herein to treat or improve or maintain the health of an area of skin. A system may include a topical formulation or a skin colonizer for influencing the microbiota of an area of skin. Such a system may treat, improve, maintain, or influence a desired, intended area of the user's skin.

A system may include a topical formulation, or a topical skin colonizer, that may comprise an oil matrix that may comprise effective amounts of jojoba oil, beeswax oil, borage oil, hemp oil, kukui oil, marula oil, perillia oil, grape seed oil, Sea Buckthorn oil, ceramides, tocopherals, vanillin, coconut oil, and vitamin D, or any appropriate combination of these components that will result in an acceptable oil matrix. The topical formulation, or topical skin colonizer, may also comprise a topical probiotic group that may comprise effective amounts of *Bacillus licheniformis, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus*, or any suitable combination of these organisms that will result in an acceptable topical probiotic group. An acceptable topical probiotic group may also include additional organisms not specified, such as *Propionibacterium jensenii, Propionibacterium freudenreichii, Roseomonas mucosa*, and the like. An acceptable topical probiotic group may also include one or more bacteriophage. A bacteriophage may be chosen that will help promote eubiosis, or put another way, a bacteriophage may be chosen that will attack those organisms that are causing or influencing dysbiosis.

A topical formulation, or topical skin colonizer, may be applied to an area of skin in any suitable manner. Such an application process may include using a swab or some other material, and may also include the user applying the topical skin colonizer with their hand or fingers.

Use of a topical formulation, or topical skin colonizer, may be influential in changing the microbiota of the area of skin. An appropriate topical formulation and/or an appropriate oral formulation may be utilized to bring about almost any desired change in the microbiota.

An appropriate topical formulation, or topical skin colonizer, may be used to change a state of dysbiosis to a state of eubiosis. It may also be use to maintain a state of eubiosis.

In one embodiment, a system may include an oral formulation that may comprise a prebiotic matrix that may comprise effective amounts of Igy-immunoglobulin, fructooligosaccharides, deoxnoiirimycin polysaccharide (DPM), carotenoids, and polyphenolic, or any appropriate combination of these components that will result in an acceptable prebiotic matrix. The oral formulation may also comprise an oral probiotic group that may comprise effective amounts of *Bacillus licheniformis, Bifidobacterium bifidum, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus*, or any suitable combination of these organisms the will result in an acceptable oral probiotic group. An acceptable oral probiotic group may also include additional organisms not specified, such as *Propionibacterium jensenii, Propionibacterium freudenreichii, Roseomonas mucosa*, and the like. An acceptable oral probiotic group may also include one or more bacteriophage. A bacteriophage may be chosen that will help promote eubiosis, or put another way, a bacteriophage may be chosen that will attack those organisms that are causing or influencing dysbiosis.

A topical formulation and an oral formulation may be utilized at approximately the same time. Such use provides a synergistic affect to positively influence the microbiota of an intended, desired area of skin.

The present invention may be embodied in other specific forms and combinations without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A product system for treating dysbiosis of the skin of a subject comprising:
   a topical formulation comprising:
      an oil matrix comprising effective amounts of jojoba oil, beeswax oil, borage oil, hemp oil, kukui oil, marula oil, perillia oil, grape seed oil, Sea Buckthorn oil, ceramides, tocopherals, vanillin, coconut oil, and vitamin D; and a topical probiotic group comprising effective amounts of *Bacillus licheniformis, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus.*

2. The product system for treating dysbiosis of the skin of said subject of claim 1, further comprising:
   an oral formulation comprising:
      a prebiotic matrix comprising effective amounts of Igy immunoglobulin, fructooligosaccharides, deoxnoirimycin polysaccharide (DPM), carotenoids, and polyphenolic; and
      an oral probiotic group comprising effective amounts of *Bacillus licheniformis, Bifidobacterium bifidum, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus.*

3. The product system for treating dysbiosis of the skin of said subject of claim 2, wherein the topical probiotic group and the oral probiotic group further comprise a bacteriophage that infects an organism contributing to the dysbiosis.

4. The product system for treating dysbiosis of the skin of said subject of claim 2, wherein the topical probiotic group and the oral probiotic group further comprise *Propionibacterium jensenii*, and *Propionibacterium freudenreichii* and *Roseomonas mucosa.*

5. A method for treating dysbiosis of the skin of a subject, comprising:
   providing an area of skin having a microbiota and a state of dysbiosis;
   providing a topical skin colonizer comprising:
      an oil matrix comprising effective amounts of jojoba oil, beeswax oil, borage oil, hemp oil, kukui oil, marula oil, perillia oil, grape seed oil, Sea Buckthorn oil, ceramides, tocopherals, vanillin, coconut oil, and vitamin D; and
      a topical probiotic group comprising effective amounts of *Bacillus licheniformis, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus;*
   applying the topical skin colonizer to the area of skin;
   changing the microbiota of the area of skin by reducing the number of organisms promoting dysbiosis and increasing the number of organisms promoting eubiosis; and
   changing the state of dysbiosis to a state of eubiosis.

6. The method for treating dysbiosis of the skin of said subject of claim 5, further comprising:
   providing an oral formulation comprising:
      a prebiotic matrix comprising effective amounts of Igy immunoglobulin, fructooligosaccharides, deoxnoirimycin polysaccharide (DPM), carotenoids, and polyphenolic; and
      an oral probiotic group comprising effective amounts of *Bacillus licheniformis, Bifidobacterium bifidum, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus;*
   ingesting the oral formulation;
   changing the microbiota of the area of skin by reducing the number of organisms promoting dysbiosis and increasing the number of organisms promoting eubiosis; and
   changing the state of dysbiosis to a state of eubiosis.

7. The method for treating dysbiosis of the skin of said subject of claim 5, wherein the resultant microbiota of the area of skin is less than about 10% Firmicutes.

8. The method for treating dysbiosis of the skin of said subject of claim 6, wherein the resultant microbiota of the area of skin is less than about 10% Firmicutes.

9. The method for treating dysbiosis of the skin of said subject of claim 6, wherein the topical probiotic group and the oral probiotic group further comprise *Propionibacterium jensenii*, and *Propionibacterium freudenreichii.*

10. The method for treating dysbiosis of the skin of said subject of claim 6, wherein the oral probiotic group further comprises a bacteriophage that infects an organism contributing to the dysbiosis.

11. The method for treating dysbiosis of the skin of said subject of claim 9, wherein the oral probiotic group further comprises a bacteriophage from the family Siphoviridae, a bacteriophage from the family Podoviridae, and a bacteriophage from the family Myoviridae.

12. The method for treating dysbiosis of the skin of said subject of claim 5, wherein the applying is done twice a day.

13. The method for treating the skin of said subject of claim 6, wherein the microbiota of the area of skin is changed from comprising about 42% Firmicutes and about 9% Actinobacteria to comprising about 6% Firmicutes and about 47% Actinobacteria.

14. The method for treating the skin of said subject of claim 6, wherein the topical probiotic group and the oral probiotic group further comprise *Propionibacterium jensenii*, and *Propionibacterium freudenreichii* and *Roseomonas mucosa.*

15. The method for treating the skin of said subject of claim 6, wherein the oral probiotic group further comprises a bacteriophage that infects an organism contributing to the dysbiosis.

16. The method for treating the skin of said subject of claim 15, wherein the oral probiotic group further comprises a bacteriophage from the family Siphoviridae, a bacteriophage from the family Podoviridae, and a bacteriophage from the family Myoviridae.

* * * * *